(12) United States Patent
Hicks et al.

(10) Patent No.: US 7,759,468 B1
(45) Date of Patent: Jul. 20, 2010

(54) BIOACTIVE PEPTIDE-BASED PROBES

(75) Inventors: Clair L. Hicks, Nicholasville, KY (US); Peter Anthony Crooks, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 814 days.

(21) Appl. No.: 10/795,174

(22) Filed: Mar. 5, 2004

Related U.S. Application Data

(60) Provisional application No. 60/452,122, filed on Mar. 5, 2003.

(51) Int. Cl.
  *C07K 1/00* (2006.01)
(52) U.S. Cl. ............. 530/402; 530/345; 530/409; 530/410
(58) Field of Classification Search .............. None
  See application file for complete search history.

(56) References Cited

U.S. PATENT DOCUMENTS

| | | | |
|---|---|---|---|
| 5,106,762 A * | 4/1992 | Bredehorst et al. | 436/546 |
| 5,612,182 A * | 3/1997 | Pearson et al. | 435/6 |
| 6,218,160 B1 * | 4/2001 | Duan | 435/188 |
| 6,416,758 B1 * | 7/2002 | Thorpe et al. | 424/145.1 |
| 6,440,419 B1 * | 8/2002 | Hein et al. | 424/178.1 |
| 2004/0121403 A1 * | 6/2004 | Miller | 435/7.1 |

FOREIGN PATENT DOCUMENTS

WO  02/061117  *  8/2002

OTHER PUBLICATIONS

Jarvis et al (Int. Dairy Journal, 5:963-976, 1995).*
Messeri et al, Journal of Bioluminescence and Chemiluminescence, 4:154-158, 1989.*
Wood et al, Methods in Enzymology, 133:354-365, 1986.*
Surjawan et al. Inhibition of *Lactococcus lactis* ssp. lactis c2 bacteriophage proliferation in *L. lactis* ssp lactis c2 grown in medium containing heat treaeted *L. lactis* ssp. lactis c2 phage-peptide. J. Dairy Sci. 83 (Suppl. 1): 92 (Abst. 395). 2000.
Surjawan et al. Inhibition of *Lactobacillus plantarum* yit 0068 bacteriophage proliferation in *L. plantarum* host grown in medium containing *Lactococcus lactis* ssp. lactis c2 phage peptide. Inst. Food Technol. Annual Meeting Book of Abstracts. (Abst. 65C-8) pp. 147. 2000.
Jose et al. Inhibition of *Lactobacillus plantarum* yit 0068 bacteriophage proliferation in *L. plantarum* host grown in medium containing *L. plantarum* yit 0068 phage peptide. Inst. Food Technol. Annual Meeting Book of Abstracts. (Abst. 65C-10) pp. 147. 2000.
Hicks et al. Effect of c2 phage peptides on *Lactococcus lactis* ssp. lactis c2 agglutination. J. Dairy Science 82 (Suppl. 1) :10. 1999.
Hicks et al. Development of bioactive probes derived from bacteriophage. 1st Annual KY Innovation and Enterprise Conference Proc., Mar. 4, 2003.
Hicks et al. Use of Hydrolized Whey peptide to inhibit culture agglutination. J. dairy Sci 83. 2000. pp. 1196-1202.

* cited by examiner

*Primary Examiner*—Patricia A Duffy
(74) *Attorney, Agent, or Firm*—King & Schickli, PLLC

(57) ABSTRACT

A method for preparing a site-specific peptide probe, wherein the peptide is specific to a receptor, includes modifying a marker to include a tether molecule and covalently binding the tether molecule to the peptide. The present invention also provides a labeled probe, comprising a peptide specific for a receptor and a marker. The marker is modified to include a tether molecule capable of covalently binding to the peptide. The peptide is typically derived from a bacteriophage or is a synthetic analog or derivative of the peptide. The receptor will typically be found on a surface of a bacterial cell. The method and probe of the invention are suitable for a rapid assay for a bacteria in a complex mixture.

12 Claims, 2 Drawing Sheets

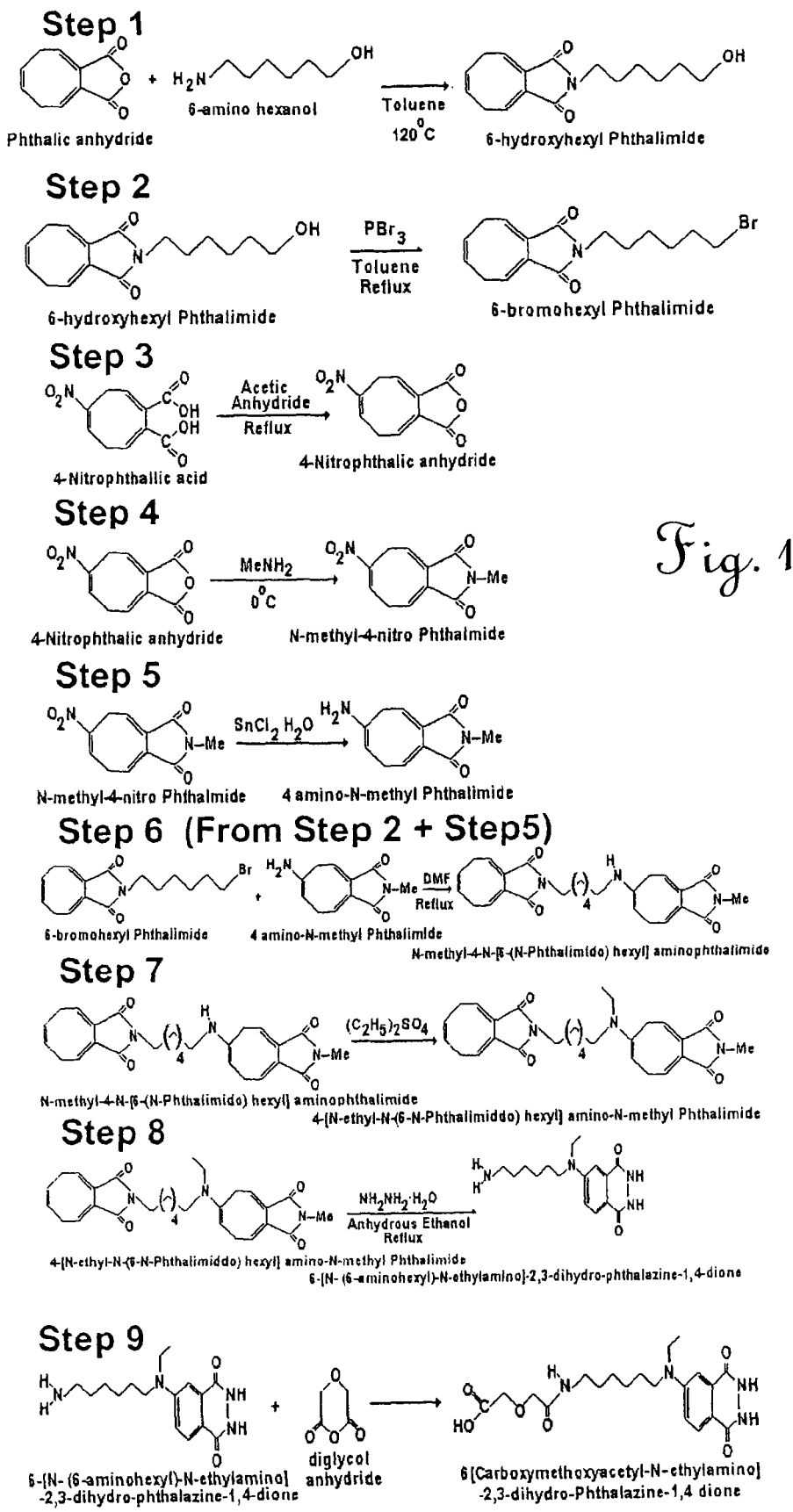

BIOACTIVE PEPTIDE-BASED PROBES

This application claims the benefit of U.S. Provisional Patent Application Ser. No. 60/452,122, filed Mar. 5, 2003.

TECHNICAL FIELD

The present invention relates to marker systems utilizing peptides. In particular, the invention relates to use of bioactive peptide probes labeled with desired marker molecules. The probes are useful in a number of assays, for example as part of a rapid cell detection system. The peptides are specific to receptors on bacterial cells, and may be derived from hydrolysis of bacteriophage cells or synthetic analogs or derivatives thereof.

BACKGROUND OF THE INVENTION

Many new rapid assays for microorganisms have been developed during the last decade. For example, two of the most sensitive tests on the commercial market are based on nucleic acid probes and the Polymerase Chain Reaction (PCR) assay. Most other tests such as radioimmunoassay and ELISA require significantly higher levels of specific bacteria for enumeration. Thus, when samples with low counts are assayed by RIA or ELISA, an enrichment step is necessary.

Nucleic acid probes consist of DNA sequences from a target bacteria that are used to detect homologous sequences of bacterial DNA or RNA. Generally, the DNA of the probe contains a radioisotope (e.g. $^{32}P$, $^{3}H$, $^{125}I$, or $^{14}C$) or other reporter molecule. When the probe DNA hybridizes with the bacterial DNA/RNA, hybridization can be detected. Detection limits can be as low as $10^4$ cfu/g, but are best when detecting $10^6$ to $10^7$ cfu/g. Nucleic acid probe based methods are problematic in the limited number of probes, the sample preparation time, enrichment time, and the complexity of the process. Thus this detection method has not been utilized by commercial industries or medical laboratories.

PCR techniques more suited to identification of microorganisms rather than enumeration, but detection limits may be as low as a single cell in purified media even in a mixed bacterial cell population. However, some compounds impede the amplification process of PCR techniques and limit the sensitivity to greater than $10^4$ cfu/ml. For example, PCR hybridization has been reported to be impeded in the presence of fermented solids such a cheese or whey. Also, many PCR assays require a 12 hour or overnight pre-enrichment step plus the time for hybridization. The complexity of the hybridization step tends to limit the procedure to a sophisticated facility such as a research laboratory. Thus the process time and complexity of the process limits the use of this procedure by many industrial and medical laboratories.

Factors that affect the commercial use of a rapid assay include: difficulty of sample preparation, time required to enrich the bacteria in question, sensitivity of the assay, time required to complete the assay, and cost. Most food and medical rapid assays are limited by the sample preparation time and the assays sensitivity in a "dirty" system (i.e., a system such as a fluid containing solids or slight turbidity). Therefore, there is a need in the art for a rapid assay for microorganisms for use in a relatively "dirty" system. The rapid assay should have the features of high sensitivity and low preparation and assay time.

Many viruses or bacteriophages have been studied, characterized, and used to develop commercial antiviral products. Fluorescent reporters or markers have been bound to bacteriophages as an assay for host bacterial organisms. However, the saturation of the dye or marker on the surface of the bacteriophage and the number of bacteriophage that bind with the host cell is variable. Accordingly, the use of bacteriophages to deliver a marker to a host cell for rapid assay purposes has not been extensively commercialized.

It is known to use peptides derived from bacteriophages in a variety of useful applications. For example, U.S. Pat. No. 6,297,042 for CHEESE MAKING WITH BACTERIOPHAGE RESISTANT BACTERIA, incorporated herein by reference, describes a method for reducing bacteriophage attack on bacteria used in the cheese making industry. The method of the '042 patent comprises addition of "blocker" peptides derived by enzymatic treatment of immunoglobulins, bacteriophages, bacteriophage parts, or mixtures thereof. Similarly, peptides derived by hydrolysis of whey proteins have been used to inhibit culture agglutination (clumping and chaining of cells) (Ustunol, Z. and C. L. Hicks. 1994. Use of an enzyme-treated, whey-based medium to reduce culture agglutination. J. Dairy Sci. 77:1479-1486; Hicks, C. L., C. E. Onuorah, and I. Surjawan. 2000. Use of hydrolyzed whey peptides to inhibit culture agglutination. J. Dairy Sci. 83:1196-1202; both incorporated herein by reference), prevent binding of intact immunoglobulins (Hicks, C. L. and Z. Tabeidie. 1998. Effect of homogenization on immunoglobulins' agglutination response in presence of lactic cultures. J. Dairy Sci. 81(Suppl. 1):32; Tabeidie, Z. and C. L. Hicks. 1998. Effect of heat treatment on immunoglobulins' agglutination response in presence of lactic cultures. J. Dairy Sci. 81(Suppl. 1):32; both incorporated herein by reference), and block bacteriophage adsorption and inhibit bacteriophage proliferation (Hicks, C. L., C. E. Onuorah, and I Surjawan. 2002. Use of hydrolyzed whey peptides to inhibit *Lactococcus lactis* ssp. *cremoris* wwa phage proliferation. J. Dairy Sci. 84:Submitted; U.S. Pat. No. 6,297,042; both incorporated herein by reference). Peptides derived from ficin hydrolysis of bacteriophage (φc2) were shown to inhibit growth of *Lactococcus lactis* ssp. *lactis* C2 (Hicks, C. L., P. A. Clark-Safko, I. Surjawan, and J. O'Leary. 2004. Use of bacteriophage-derived peptides to delay phage infections. Food Res. Intl. 37 (2):115-122; incorporated herein by reference).

The present invention addresses the identified need in the art by providing bioactive probes comprising peptides labeled with a marker. Typically, the peptides are attachment peptides derived from bacteriophages, or are synthesized analogs or derivatives which correspond to such attachment peptides and to bind to the same receptor molecules. It is known that attachment peptides of various bacteriophages can range across genus (i.e. peptide sequences that bind to calcium receptors), or can be limited to individual strains (i.e. peptide sequences specific to multiple carbohydrate moieties of a particular bacterial cell wall). Thus, peptide-based probes are provided, attached to a marker, which deliver the marker to the surface of a specifically targeted bacteria where the concentration of the marker can be quantified. Further, a method for detecting a bacteria is provided, comprising attaching a detectable molecule to a smaller bacteriophage peptide or synthetic bacteriophage peptide which binds to specific host bacteria, thereby increasing saturation of the marker and improving sensitivity of the assay.

SUMMARY OF THE INVENTION

In accordance with the purposes of the present invention as described herein, a method is provided for preparing a site-specific peptide probe, comprising modifying a marker to include a tether molecule, wherein the peptide is specific to a receptor and the tether molecule is capable of covalently binding to the peptide, and covalently binding the tether molecule to the peptide. The tether molecule may be adapted to covalently bind to the primary amine or to the carboxyl end of the peptide. Typically, the receptor will be found on a surface of a bacterial cell, such as for example the F protein receptor. The peptide may include an N terminal sequence ( . . . Ala-Glu-Leu-Glu, SEQ ID NO: 1; Ala-Lys-Glu-Lys-Tyr-Val-Ile-Gln-Ala-Glu-Leu-Glu, SEQ ID NO: 3) or a calcium binding sequence (Ser-Asn-Glu-Glu-Met . . . ; SEQ ID NO: 2) of the F protein.

The peptide may be produced by hydrolysis of a bacteriophage. The bacteriophage may be selected from the group of bacteriophages specifically binding to *Lactobacillus, Lactococcus, Salmonella, Escherichia*, and mixtures thereof. The bacteriophage may be selected from the group of bacteriophages specifically binding to *Lactobacillus plantarum* species, *Lactococcus lactis* species, *Salmonella typhimurium* species, *Salmonella choleraesuis* species, *Escherichia coli* species, and mixtures thereof.

In one embodiment, the peptide is derived by hydrolyzing a bacteriophage with a protease enzyme. The protease may be selected from a group consisting of papain, bromelain, ficin, pepsin, trypsin, chymotrypsin, and mixtures thereof. In another embodiment, the peptide may be a synthetic analog or derivative of a bacteriophage peptide. Still further, the peptide may be Lys-Lys-Lys, Glu-Glu, or a mixture thereof.

The marker may be selected from the group consisting of a luciferin compound, a luminol compound, and mixtures thereof, the luciferin compound and luminol compound being modified to include a tether molecule. In one embodiment, the marker is 6-[carboxymethoxyacetyl-N-(6-aminohexyl)-N-ethylamino]-2,3-dihydro-phthalazine-1,4-dione or 6-[N-(6-aminohexyl)-N-ethylamino]-2,3-dihydro-phthalazine-1,4-dione.

In another aspect of the present invention, a labeled probe is provided, comprising a peptide specific for a receptor, the peptide being derived from a bacteriophage or a synthetic analog or derivative of the peptide, and a marker. As described above, the marker is modified to include a tether molecule capable of covalently binding to the peptide. The peptide is typically specific to a receptor on a bacterial cell wall. The tether molecule may be capable of covalently binding to a primary amine of the peptide or to a carboxyl end of the peptide. Other features of the peptide, marker, and receptor are as described above.

In yet another aspect, the present invention provides a method for detecting a bacterium in a complex mixture, comprising contacting the bacterium with a labeled probe as described above. The method is suited to a rapid assay technique for bacteria in a complex mixture, such as for example a milk or whey preparation used in cheesemaking.

As should be appreciated, the embodiments shown and described are an illustration of one of the modes best suited to carry out the invention. It will be realized that the invention is capable of other different embodiments and its several details are capable of modification in various, obvious aspects all without departing from the invention. Accordingly, the drawings and descriptions will be regarded as illustrative in nature, and not as restrictive.

BRIEF DESCRIPTION OF THE DRAWINGS

The accompanying drawings incorporated in and forming a part of the specification, illustrate several aspects of the present invention and together with the description serve to explain the principles of the invention. In the drawings:

FIG. 1 schematically depicts synthesis of a tether molecule on a luminol marker for covalently binding to a peptide.

Figure 2A:
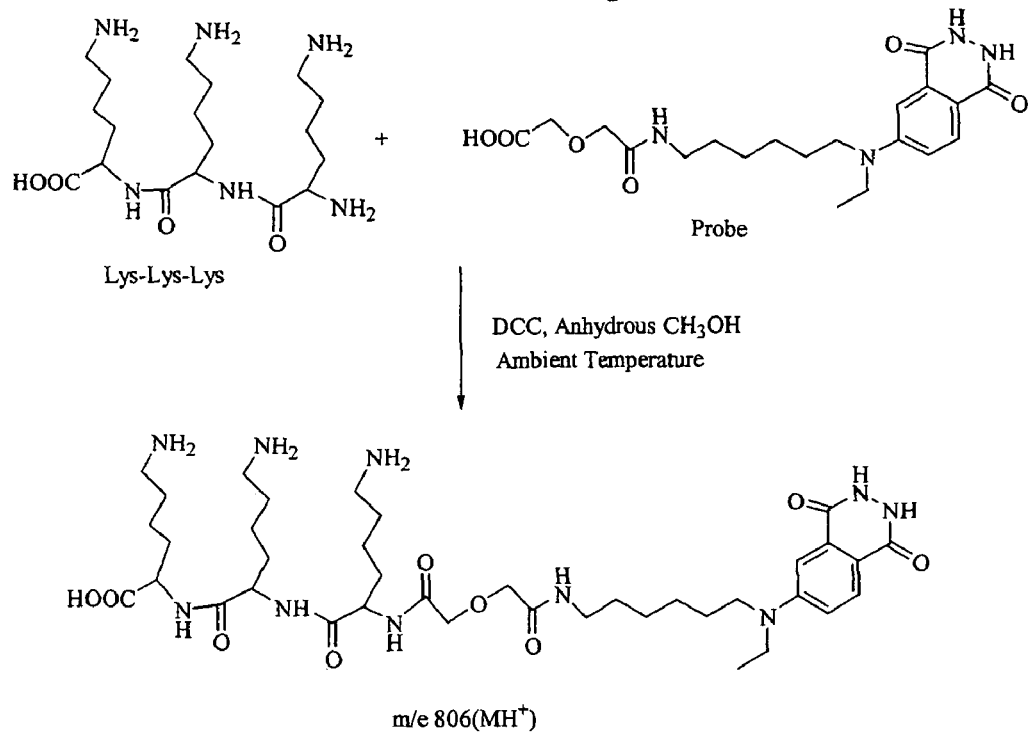
FIGS. 2a and 2b schematically depict conjugation of a tri-lysine peptide (2a) and a Glu-Glu peptide (2b) to the compound of FIG. 1.

Reference will now be made in detail to the present preferred embodiment of the invention, an example of which is illustrated in the accompanying drawings.

DETAILED DESCRIPTION OF THE INVENTION

Methods of binding/interaction between many bacteria and bacteriophages are well characterized. For example, the non-pathogenic *Lactococcus lactis* ssp. *lactis* C2 host and φc2 bacteriophage are one of the best characterized host/phage systems in the literature (Kraus, J. and B. L. Geller. 1998. Membrane Receptor for prolate phages is not required for infection of *Lactococcus lactis* by small or large isometric phages. J. Dairy Sci. 81:2329-2335; Lubbers, M. W., N. R. Waterfield, T. P. J. Beresford, R. W. F. LePage, and A. W. Jarvis. 1995. Sequencing and analysis of the prolate-headed lactococcal bacteriophage c2 genome and identification of the structural genes. Appl. Environ. Microbiol. 61:4348-4356). In particular the peptides responsible for binding of many bacteriophages to bacteria have been isolated, characterized, and sequenced. As an example, the binding protein in the membrane of the C2 host and its corresponding gene (pip) have been identified (Kraus and Geller, 1998). This 99 kDa membrane protein contains the receptor configuration that the φc2 phage binds to irreversibly. Also, the attachment protein (protein F) of the φc2 phage has been identified and partially sequenced (Lubbers et al., 1995). Both the N-terminal and calcium binding sites of the φc2 phage F protein have been identified (Lubbers et al., 1995). Thus, probes for rapid assay of bacteria in a mixture can be developed from viral sources by taking advantage of the specificity of these attachment proteins, and more specifically of the peptides specifically responsible for binding. The present invention therefore provides bioactive probes comprising such peptides and a marker molecule. The peptide and marker are bound by a tether molecule, which is important in distancing the marker from the peptide receptor to prevent steric hindrance of binding of subsequent bioactive probes and concomitant reduction in assay sensitivity.

The following examples are presented in support of and to further illustrate the invention as described above, but are not to be considered as limited thereto.

EXAMPLE 1

A process was developed to prepare a site-specific probe, comprising modification of a marker by addition of a tether molecule capable of covalently binding to a peptide. The peptide is desirably specific for a receptor on a surface of a target bacteria. The process is depicted schematically in FIG. 1. In this experiment, the detectable molecule was luminol (phthalic anhydride). Phthalic anhydride (11.7 g, 100 mmol) and 6-amino hexanol (14.8 g, 100 mmol) were admixed with 120 ml anhydrous toluene in a flask fitted with Dean-Stork apparatus and refluxed for 12 hr. at 120° C. The water formed was removed as an azeotrope. Toluene was removed using rotavapor. A flash column chromatography was performed over silica gel (230-400 mesh) with ethyl acetate and petroleum ether as eluant. The yield of the resulting 6-hydroxyl phthaliamide compound was 22.7 g (92%), Mp 49-50° C.

To 6-hydroxyl phthaliamide (22.5 g, 0.09 mole) in 100 ml of anhydrous toluene at 110° C. was added phosphorous tribromide (17 g, 0.063 mole). The phosphorous tribromide was taken in 20 ml of anhydrous toluene and added slowly through a pressure equalizing funnel. The mixture was refluxed for 3 hours and allowed to cool to room temperature. The orange precipitate formed was removed by filtering through celite. The filtrate was then concentrated in a rotavac to obtain an oil. The oil was crystallized using absolute ethanol to yield 6-bromohexylphthalimide of analytical purity ((25.1 g (90%), Mp 59-60° C.)).

Next, 4-nitrophthalic acid (21.1 g, 0.1 mole) in a round-bottomed flask was admixed with acetic anhydride (40 ml) and refluxed for 1 hour. The mixture was brought to room temperature and acetic anhydride was removed under vacuum. The concentrated mixture was allowed to stand overnight, and the solid obtained was recrystallized using toluene to give 4-nitrophthalic anhydride ((9.9 g (51%), Mp 119° C.)).

The 4-nitrophthalic anhydride (9.5 g, 49.2 mmol) was combined with 20 ml of 33% methylamine solution in absolute ethanol in a round-bottomed flask and stirred for 2 hours at 0° C. The mixture was acidified to pH 2.0 with concentrated HCl, and concentrated under vacuum. The solid obtained was refluxed with 20 ml acetic anhydride for 15 min. and allowed to stand overnight. The crystals obtained were washed with acetic acid, water, and dried. Thin layer chromatography of the mother liquor indicated that a product was present. The mother liquor was evaporated, and the resulting slurry was subjected to flash column chromatography over silica gel (240-300 mesh) with ethyl acetate and petroleum ether as eluant. Yield of N-methyl-4-nitrophthalimide was 4.9 g (48%), Mp 177° C.

To a solution of $SnCl_2$ dihydrate (19.2 g, 85 mmol) in 8 ml water and 24 ml concentrated Hcl was added N-methyl-4-nitrophthalimide (4.5 g, 21.8 mmol). The mixture was stirred vigorously for 2 hours, and allowed to stand overnight. The mixture was then concentrated to ¾ original volume using rotavapor. The solid obtained was filtered and washed with water several times. The solid was dried to give 4-amino-N-methylphthalimide ((2.1 g (54.7%), Mp 247-248° C.).

Next, to 6-bromohexylphthalimide (7.04 g, 22.7 mmol) in 20 ml of anhydrous DMF under nitrogen atmosphere was added 4-amino-N-methylphthalimide (4 g, 22.7 mmol). The mixture was stirred under nitrogen at 120° C. for 30 hr. The reaction mixture was then cooled to room temperature, placed in ice-cold water and stirred. The resulting yellow precipitate was filtered and recrystallized from aqueous acetic acid. Yield of N-methyl-4-N-{6-(N-phthalimidio)hexyl])aminophthalimide was 4.5 g (49%), Mp 169-170° C.

Next, N-methyl-4-N-{6-(N-phthalimidio)hexyl])aminophthalimide (3.7 g, 9.2 mmol) was admixed with diethyl sulfate (11 ml, 70.84 mmol) in a flask under nitrogen. This mixture was gradually heated with stirring at 110° C. for 2 hr. The temperature was then raised to 160° C. and kept for 20 min. A brown color developed. The mixture was then cooled to room temperature, poured into ice cold water, and stirred. The yellow precipitate was filtered and recrystallized from aqueous acetic acid. Yield of 4-[N-ethyl-N-(6-N-phthalimido)hexyl]amino-N-methyl phthalimide was 2.3 g (58%), Mp 195-196° C.

To 4-[N-ethyl-N-(6-N-phthalimido)hexyl]amino-N-methyl phthalimide (1.75 g, 4.04 mmol) in 20 ml absolute ethanol under nitrogen was added hydrazine (5 ml, 147.1 mmol). The reaction mixture was refluxed for 3 hr under nitrogen. The solvent was removed under vacuum, and the solid dried at 110° C. under vacuum. The residue was dissolved in 10% HCl and filtered. The filtrate was adjusted to pH 8 using potassium hydroxide. The resulting 6-[N-(6-aminohexyl)-N-ethylamino]-2,3-dihydro-phthalazine-1,4-dione precipitate was filtered and crystallized from aqueous dimethylformamide (DMF). Yield was 220 mg (18%).

Finally, 6-[N-(6-aminohexyl)-N-ethylamino]-2,3-dihydro-phthalazine-1,4-dione (608 mg, 2 mmol) in 10 ml anhydrous DMF under nitrogen was admixed with diglycolic anhydride (232 mg, 2 mmol) and triethylamine (205 mg, 2 mmol). The reaction mixture was stirred under nitrogen for 18 hr. The solvent was removed under vacuum and the oil obtained was dissolved in anhydrous methanol and kept at 4° C. for crystallization. Yield of 6-[carboxymethoxyacetyl-N-(6-aminohexyl)-N-ethylamino]-2,3-dihydro-phthalazine-1,4-dione was 420 mg (50%). This product is then reacted with the primary amine of a peptide derived from a bacteriophage, or a synthetic analog or derivative of the peptide, to form a fluorescently labeled peptide specific to the receptor of choice. If it is desired to bind the marker to the carboxyl end of the peptide, then the 6-[N-(6-aminohexyl)-N-ethylamino]-2,3-dihydro-phthalazine-1,4-dione is reacted with the peptide. The marker includes a 6 carbon tether molecule, which binds to the peptide, thereby providing a distance between the marker and the peptide when the peptide binds to a receptor on a bacterial cell surface.

EXAMPLE 2

To standardize the reaction conditions, the isoluminol marker synthesized as described in Example 1 was coupled with low molecular weight synthesized peptides. Two peptides, Lys-Lys-Lys and Glu-Glu were selected. The tri-lysine peptide was selected due to the availability of several amine attachment sites. Glu-Glu was selected due to its carboxyl sites. Both peptides were reacted with the reporter molecule 6-[carboxymethoxyacetyl-N-(6-aminohexyl)-N-ethylamino]-2,3-dihydro-phthalazine-1,4-dione, prepared as described in Example 1. Purified probes were tested using mass spectrometry (Maldi method) and proton and carbon nuclear magnetic resonance (NMR).

Figure 2B:
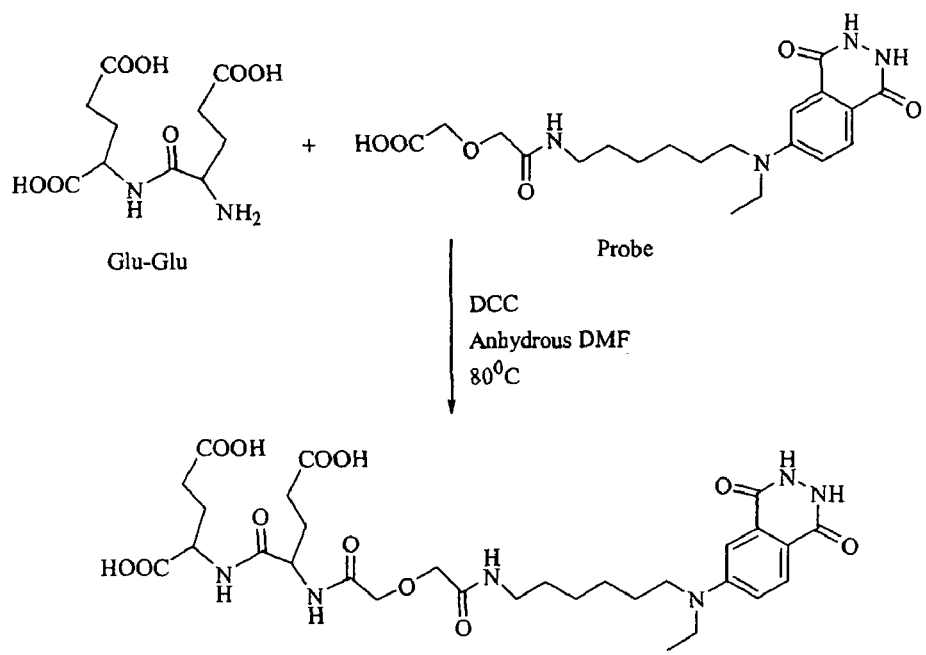

As depicted schematically in FIG. 2, the tri-lysine peptide was reacted with 6-[carboxymethoxyacetyl-N-(6-aminohexyl)-N-ethylamino]-2,3-dihydro-phthalazine-1,4-dione in the presence of dicyclohexylcarbodiimide (DCC) and anhydrous methanol at ambient temperature under nitrogen. NMR spectra showed that the resulting probe was a single positional isomer. Mass spectrometry indicated that the monomer had a molecular weight of 805, corresponding to the molecular ion of the monoconjugated product. A small amount of tri-lysine reacted with two reporter molecules (less than 0.5%), and had a molecular weight of 1208. Although not wishing to be bound to any particular theory, because a single positional isomer was formed the reaction between the tri-lysine and the reporter molecule may have occurred between the peptide primary amine and the terminal carboxyl group of the reporter. Importantly, successful binding of the tri-lysine peptide to the reporter indicated that blockers on the ε-amine were unnecessary to produce the desired bioactive probe.

EXAMPLE 3

The glu-glu peptide was reacted with 6-[carboxymethoxyacetyl-N-(6-aminohexyl)-N-ethylamino]-2,3-dihydro-phthalazine-1,4-dione in the presence of dicyclohexylcarbodiimide (DCC), anhydrous methanol, and a few drops of DMF at 75-80° C. NMR spectra showed that the resulting probe was a single positional isomer. Mass spectrometry indicated that the methylated monomer had a molecular weight of 707. Although not wishing to be bound to any particular theory, because a single positional isomer was formed, the reaction between the Glu-Glu peptide and the reporter molecule may have occurred between the primary amine and the terminal carboxyl group of the probe.

The Glu-Glu peptide is known to be a potent inhibitor of growth for *L. lactis* ssp. *lactis* C2 and other lactic acid bacteria having calcium binding receptors on their outer membrane. Accordingly, the bioactive Glu-Glu probe synthesized herein is expected to bind well to all gram positive bacteria having calcium binding receptors.

EXAMPLE 4

The Glu-Glu probe of Example 3 was produced, with the exception that the coupling reaction was carried out in anhydrous DMF without methanol to prevent formation of the dimethyl ester of the coupled monoconjugated product.

EXAMPLE 5

A bio-active probe highly specific to *Lactococcus lactis* ssp *lactis* C2 was provided. The N-terminal sequence of amino acids from the c2 phage F protein are highly specific to the receptors on the outer membrane of *L. Lactis* ssp *lactis* C2. Thus, by combining the N-terminal sequence of amino acids from the c2 phage F protein to the marker produced as described in Example 1, the probe is highly specific for the C2 *lactis* strain. The specific amino acid sequence can be derived from the F protein, from a genetically engineered source, or synthesized commercially. The primary amine of Glu was then covalently bound to the carboxyl end of the tethered reporter molecule as shown below.

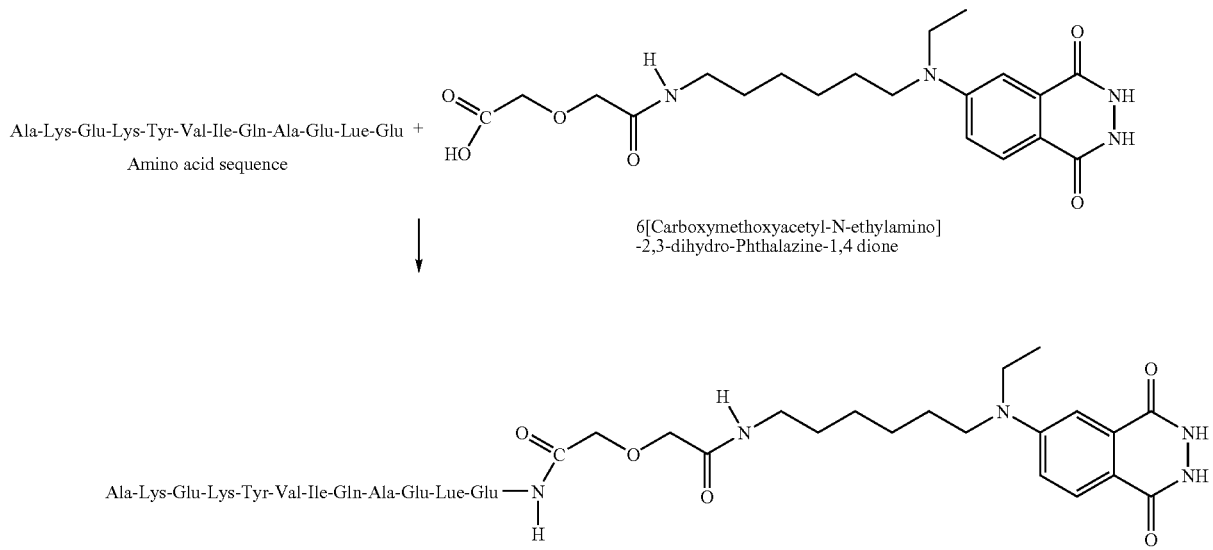

The bio-active probe produced by this procedure was added in excess to C2 bacteria at concentrations of $10^2$, $10^3$, and $10^4$ cfu/ml. The bio-active probe was then allowed to absorb onto the surface of the C2 bacteria for 20 min. The bacteria were spun down (5000×g for 10 min), the pellet was suspended and washed with phosphate dilution buffer, spun down again, and washed a second time as before. The pellet was suspended in phosphate buffer and fluorescence from the bio-active reporter molecule was determined using a GENios Plus™, a multi-detection microplate reader. The following data were collected from the reader using an appropriate blank.

| Concentration of C2 bacteria | Fluorescence |
| --- | --- |
| $10^4$ cfu/ml | 0.114 |
| $10^3$ cfu/ml | 0.072 |
| $10^2$ cfu/ml | 0.058 |

This suggests that bacteria in concentrations as low as $10^2$ cfu/ml could be determined using this method.

The foregoing description of the preferred embodiment of this invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for preparing a site-specific peptide probe, wherein the peptide is specific to a receptor, comprising:
  modifying a 6-[N-(6-aminohexyl)-N-ethylamino]-2,3-dihydro-phthalazine-1,4-dione marker to include an amino-terminal carboxymethoxyacetyl tether molecule; and
  covalently binding the tether molecule to a bacteriophage-derived peptide or synthetic peptide which binds a bacterial surface receptor therefor.

2. The method of claim 1, wherein the receptor is the bacteriophage F protein receptor.

3. The method of claim 2, wherein the peptide consists of Ala-Glu-Leu-Glu (SEQ ID NO: 1), Ser-Asn-Glu-Glu-Met (SEQ ID NO: 2), Ala-Lys-Glu-Lys-Tyr-Val-Ile-Gln-Ala-Glu-Leu-Glu (SEQ ID NO: 3), Lys-Lys-Lys, or Glu-Glu.

4. The method of claim 2, wherein the bacteriophage is selected from the group of bacteriophages specifically binding to *Lactobacillus, Lactococcus, Salmonella, Escherichia*, and mixtures thereof.

5. The method of claim 4, wherein the bacteriophage is selected from the group of bacteriophages specifically binding to *Lactobacillus plantarum* species, *Lactococcus lactis* species, *Salmonella typhimurium* species, *Salmonella choleraesuis* species, *Escherichia coli* species, and mixtures thereof.

6. The method of claim 5, wherein the bacteria is *Lactococcus lactis* ssp. *lactis* C2.

7. A method for preparing a site-specific peptide probe, wherein the peptide is specific to a receptor, comprising:
  modifying a 6-[N-(6-aminohexyl)-N-ethylamino]-2,3-dihydro-phthalazine-1,4-dione marker to include an amino-terminal carboxymethoxyacetyl tether molecule; and
  covalently binding the tether molecule to a bacteriophage-derived peptide which binds a bacterial surface receptor for a bacteriophage F protein.

8. The method of claim 7, wherein the peptide consists of Ala-Glu-Leu-Glu (SEQ ID NO: 1), Ser-Asn-Glu-Glu-Met (SEQ ID NO: 2), Ala-Lys-Glu-Lys-Tyr-Val-Ile-Gln-Ala-Glu-Leu-Glu (SEQ ID NO: 3), Lys-Lys-Lys, or Glu-Glu.

9. The method of claim 7, wherein the bacteriophage is selected from the group of bacteriophages specifically binding to *Lactobacillus, Lactococcus, Salmonella, Escherichia*, and mixtures thereof.

10. The method of claim 9, wherein the bacteriophage is selected from the group of bacteriophages specifically binding to *Lactobacillus plantarum* species, *Lactococcus lactis* species, *Salmonella typhimurium* species, *Salmonella choleraesuis* species, *Escherichia coli* species, and mixtures thereof.

11. The method of claim 10, wherein the bacteria is *Lactococcus lactis* ssp. *lactis* C2.

12. A method for preparing a site-specific peptide probe, wherein the peptide is specific to a receptor, comprising:

modifying a 6-[N-(6-aminohexyl)-N-ethylamino]-2,3-dihydro-phthalazine-1,4-dione marker to include an amino-terminal carboxymethoxyacetyl tether molecule; and covalently binding the tether molecule to a bacteriophage-derived peptide or synthetic peptide which binds a bacterial surface receptor therefor;

wherein the bacteriophage-derived peptide or synthetic peptide is selected from the group consisting of Ala-Glu-Leu-Glu (SEQ ID NO: 1), Ser-Asn-Glu-Glu-Met (SEQ ID NO: 2), Ala-Lys-Glu-Lys-Tyr-Val-Ile-Gln-Ala-Glu-Leu-Glu (SEQ ID NO: 3), Lys-Lys-Lys, or Glu-Glu.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: c2 bacteriophage

<400> SEQUENCE: 1

Ala Glu Leu Glu
1

<210> SEQ ID NO 2
<211> LENGTH: 5
<212> TYPE: PRT
<213> ORGANISM: c2 bacteriophage

<400> SEQUENCE: 2

Ser Asn Glu Glu Met
1               5

<210> SEQ ID NO 3
<211> LENGTH: 12
<212> TYPE: PRT
<213> ORGANISM: c2 bacteriophage

<400> SEQUENCE: 3

Ala Lys Glu Lys Tyr Val Ile Gln Ala Glu Leu Glu
1               5                   10